(12) United States Patent
McCue et al.

(10) Patent No.: US 6,228,389 B1
(45) Date of Patent: May 8, 2001

(54) FLEXIBLE HYDROPHILIC ARTICLES HAVING A RESIDUAL ANTIMICROBIAL EFFECT

(75) Inventors: Karen Ann McCue, Tenafly; Beverly Ann Kiefer, Montvale, both of NJ (US); William Ronald Feuer, Nyack, NY (US)

(73) Assignee: Reckitt Benckiser Inc., Wayne, NJ (US)

( * ) Notice: Subject to any disclaimer, the term of this patent is extended or adjusted under 35 U.S.C. 154(b) by 0 days.

(21) Appl. No.: 09/033,918

(22) Filed: Mar. 3, 1998

(30) Foreign Application Priority Data

Apr. 2, 1997 (GB) .................................................. 9706714

(51) Int. Cl.⁷ .................................................. A61K 9/70
(52) U.S. Cl. ........................... 424/443; 428/221; 424/402; 424/404; 424/405; 521/50
(58) Field of Search ............................ 428/221; 424/402, 424/404, 405, 443; 521/50

(56) References Cited

U.S. PATENT DOCUMENTS

| | | | |
|---|---|---|---|
| 3,227,614 | 1/1966 | Scheuer | 167/84 |
| 3,283,357 | 11/1966 | Decker et al. | 15/506 |
| 3,586,520 | 6/1971 | Dillon | 106/15 |
| 4,339,550 | 7/1982 | Palinczar et al. | 521/99 |
| 4,631,297 | 12/1986 | Battice et al. | 521/78 |
| 4,666,621 | 5/1987 | Clark et al. | 252/91 |
| 4,692,374 | 9/1987 | Bouchette | 428/288 |
| 4,704,757 | 11/1987 | Young | 15/104.94 |
| 4,737,405 | 4/1988 | Bouchette | 428/288 |
| 4,740,398 | 4/1988 | Bouchette | 428/28 |
| 4,847,089 | 7/1989 | Kramer et al. | 424/405 |
| 4,877,816 | 10/1989 | Murabayahi et al. | 521/92 |
| 4,923,607 | 5/1990 | Ninomiya et al. | 210/490 |
| 5,000,987 | 3/1991 | Ninomiya et al. | 427/246 |
| 5,091,102 | 2/1992 | Sheridan | 252/91 |
| 5,152,996 | 10/1992 | Corey et al. | 424/443 |
| 5,156,843 | 10/1992 | Leong et al. | 424/411 |
| 5,173,535 | 12/1992 | Abrutyn | 525/54.3 |
| 5,180,061 | 1/1993 | Khan et al. | 206/570 |
| 5,441,742 | 8/1995 | Autant et al. | 424/405 |
| 5,541,233 | 7/1996 | Roenigk | 521/54 |

FOREIGN PATENT DOCUMENTS

| | | |
|---|---|---|
| 40969/89 | 3/1990 | (AU) . |
| 0 084 708 A1 | 8/1983 | (EP) . |
| 0 358 572 A1 | 3/1990 | (EP) . |
| 0358572 A1 | 3/1990 | (EP) . |
| 0617074 A1 | 9/1994 | (EP) . |
| 0641539 A1 | 3/1995 | (EP) . |
| 1 424 692 | 2/1976 | (GB) . |
| 2122900 | 1/1984 | (GB) . |
| 2299939 | 10/1996 | (GB) . |
| WO89/10691 | 11/1989 | (WO) . |
| WO92/21239 | 12/1992 | (WO) . |
| WO95/04459 A1 | 2/1995 | (WO) . |

OTHER PUBLICATIONS

Copy of the European Search Report for EP Application No. 98302541 dated Jul. 6, 1998.
WPI Abstract No. 95–077938 and JP 070002615A.
WPI Abstract of JP 7002615.
Copy of GB Search Report for GB Application No. 9806967.7 dated Jun. 18, 1998.
Copy of GB Patent Office Search Report for GB Application No. 9706714.4 dated Jun. 3, 1997.

Primary Examiner—Samuel A. Acquah
(74) Attorney, Agent, or Firm—Fish & Richardson P.C.

(57) ABSTRACT

Flexible wiping articles in particular sponges, as well as woven or non-woven wipes, and the like feature a long term antimicrobial benefit even subsequent to continued use. The articles comprise a biocidal composition having a low aqueous solubility. Methods for preparing the articles, and processes for their use are also disclosed.

10 Claims, No Drawings

FLEXIBLE HYDROPHILIC ARTICLES HAVING A RESIDUAL ANTIMICROBIAL EFFECT

The present invention relates to flexible wiping articles in particular sponges, as well as woven or non-woven wipes, and the like. More specifically, the present invention relates to wiping articles having a residual long-term antimicrobial effect.

Wiping articles are commonly used in the cleaning of hard surfaces including but not limited to, glass, dishes, porcelain, lavatory fixtures, kitchen fixtures and appliances, sinks, and the like are well known. These take a variety of forms, including woven and non-woven wipes formed of fibrous (natural or synthetic) materials and in particular hydrophilic sponges. These sponges may be formed from any a variety of materials including foamed polymers as well as from cellulose. These are per se well known to the art and are very commonly encountered in food service, medical, and other environments.

A consequence of the use of such materials, particularly when used in any type of a cleaning operation is that after the sponge or wiping article has been used, it is frequently set aside in a moist state. In its moist state, it provides a place for the breeding of various bacteria, viruses, fungi, etc. Thus, these sponges and wiping articles are not sanitary.

Known to the art a variety of wiping articles and sponges which have various degrees of antimicrobial benefit provided therein. These are provided by different processes or by the use of particular constituents which are used in conjunction with such sponges or wiping articles. These include, for example those described in the following patents: U.S. Pat. No. 4,666,621, U.S. Pat. No. 4,737,405, U.S. Pat. No. 4,740,398, U.S. Pat. No. 5,091,102, U.S. Pat. No. 4,692,374, U.S. Pat. No. 5,156,843, U.S. Pat. No. 3,227,614, U.S. Pat. No. 3,283,357, U.S. Pat. No. 4,847,089, U.S. Pat. No. 5,541,233, U.S. Pat. No. 5,441,742, U.S. Pat. No. 4,339,550, U.S. Pat. No. 5,173,535 and U.S. Pat. No. 4,704,757. Also, it is also known to include a minor amount of a biocide, such as a preservative composition into a sponge prior to packaging. This ensures that as the sponge is on the shelf and prior to its use it is unlikely to grow mold, fungi, or to contain bacteria or viruses prior to its use on the opening of the package by the ultimate product consumer. It is also known to the art that many types of sponges, especially cellulose sponges, are packaged and sold in a substantially dehydrated form wherein it is very unlikely that a mold, fungus, virus or bacteria will find beneficial conditions for growth.

While these sponges and wiping articles described above are known to the prior art do provide various benefits, they are not without shortcomings. One particular shortcoming which is of increasing concern to the consumer is the long-term antimicrobial efficacy of the sponge. Frequently, in sponges which are treated with small amounts of biocides, these biocides are generally washed out after even a few uses of the sponge under normal cleaning conditions. Thus, although the said sponge has been treated during its packaging stage, shortly after its use, it no longer retains any appreciable antimicrobial efficacy. Certain other sponges and wiping articles have been proposed in the art which do provide an effective antimicrobial benefit which may be of somewhat longer duration; however the methods for producing such sponges and wiping articles are frequently complicated and require additional and/or complex steps in the production of the sponge or wiping article.

Accordingly, there is a real and continuing need in the art for sponges and other wiping articles which have a useful antimicrobial benefit during a period of normal use in cleaning, wiping, and other operations. These objects are provided by the articles, processes, and methods of the present invention.

Accordingly, one aspect of the invention provides a wiping article such as a woven or non-woven wipe, or a sponge which has a residual antimicrobial effect wherein said article is impregnated with an effective amount of a low aqueous soluble biocide composition which is effective against gram positive, gram negative or most desirably is effective against both gram positive and gram negative bacteria.

According to a further aspect of the invention, there is provided a process for providing long-lasting residual antimicrobial benefit to a sponge, non-woven or woven wipe, or other wiping article which comprises the process step of:

providing a low aqueous soluble biocidal composition in an appropriate fluid carrier within which said preservative composition is miscible, but is preferably soluble;

impregnating the said wiping article to provide an effective dosage of the preservative composition to the same; and, subsequently removing at least a portion, preferably substantially all of the carrier composition.

These and other aspects of the invention will be more clearly described below.

The wiping articles useful in the present invention include those such as are commonly encountered and these specifically include sponges, preferably hydrophilic sponges, as well as woven and non-woven wiping articles. With respect to sponges, these may be any variety which are presently known and many which are widely commercially available including those produced from foamed rubbers (naturally occurring or synthetically produced), foamed polymers such as polyurethane, polypropylene, polyethylene, polyester, polyethers, and of regenerated cellulose. Sponges which are particularly useful in the compositions of the present invention are those which are formed from cellulose and are also interchangeably referred as viscose sponges. These are known to the art and are produced from comminuted and ground wood pulp which are then regenerated to form a porous hydrophilic article.

With regard to such sponges, it is to be understood that these may be of a single material and of a single layer, or they may be produced as a composite material. What is to be understood as composite material is that two or more differing materials may be combined to form a sponge where at least one layer is hydrophilic, especially a first layer of a hydrophilic material which is glued, sewn, or otherwise connected to a second layer of a differing material. Such differing materials include those which are commonly known, including those formed of woven and/or non-woven fabric materials which are often intended to provide an abrasive surface which are not particularly deleterious to soft surfaces (Teflon®, Corian®, fiberglass, etc.). Also, such composite sponges also include those which include one or two differing hydrophilic sponge materials which may be sewn together. In this sponge construction, sponges of two different materials are sewn together at peripheral edges, and further optionally on at least one face of the sponge is further included a woven textile material. Such an exemplary sponge is available as Chore Boy® Long-Last sponges (Reckitt & Colman Inc.).

With regard to woven and/or non-woven wipes, these include a variety of materials which may be formed into wipes by the knitting or weaving of fibrous materials, particularly polymeric fibrous materials including, but not limited to, polypropylene, polyethylene, polyester, polyamide, regenerated cellulosic fibers as well as those based on naturally occuring materials such as cellulose fibers particularly those which are based on wood pulp fibers as provided by either chemical and/or mechanical pulp fibers. Such fibers may alternately be formed into a non-woven web by a variety of known art techniques including inter alia, air laying and wet laying of the naturally occurring (cellulose) and/or synthetic (polymeric) fibers into a web. Further useful are non-woven materials wherein a non-woven mat of such fibrous materials are produced by providing an intermediate adhesive between the individual fibers, or by cross linking of the fibers themselves.

Further useful woven and/or non-woven wipes include those which are produced from cellulosic fibers which may be formed into a web by a variety of known art techniques, including air laying and wet laying of the fibers To such woven and/or non-woven fibers may also be added amounts of abrasive materials including one or more mineral salts including, but not limited to, metal oxides especially aluminum oxide.

It is to be understood that with regard to the description of the wiping articles, the sponges, woven and non-woven wipes described above are provided by way of illustration not by way of limitation and other materials other than described herein may also enjoy the benefits of the present invention.

With regard to the biocide composition, the inventors have surprisingly found that the use of a low-water soluble biocides may be effectively used to impregnate the wiping article, and at the same time, provide a long-term sanitizing benefit to the sponge which is effective, against gram positive, or gram negative, but most preferably against both gram positive and gram negative bacteria.

Such biocidal compositions are per se known to the art and may be available from a variety of commercial sources. Useful compositions include those which exhibit a solubility in water at 25° C. of not more than about 7.5% by weight, more preferably are those which exhibit solubility of less than about 5.5% by weight, and most preferably are those compositions which exhibit a solubility of water at 25° C. of not more than about 4% by weight, but most desirably are those having aqueous solubilities of less than about 1% by weight and even lesser aqueous solubilities. By way of non-limiting examples, these include the following commercially available preparations: Proxel® GXL (19.3%wt. actives) (Zeneca Biocides, Wilmington Del.) which is described to be a preparation which contains 1,2-benzisothiazoline-3-one as an active constituent; Dantogard® Plus (Lonza Inc., Fairlawn N.J.) which is described to be a preparation which contains DMDM Hydantoin and iodo propynyl butyl carbamate as active constituents; Busan® 1104 (93%wt. actives) (Buckman Co.) which is described to have an aqueous solubility in water of up to about 4%wt. at 25° C. and to be a preparation which contains dimethylhydroxymethylpyrazole as an active constituent; Germabeng® II (44%wt. actives) (Sutton Co., Madison N.J.) which is described to be a preparation which contains as active constituents a mixture based on diazolidinyl urea, methylparaben, propylparaben & propylene glycol; Troysan® 142 (95%wt. actives) (Troy Chemical Co.) which is described to have an aqueous solubility in water of up to about 0.12%wt. at about 30° C. and to be a preparation which contains 3,5-dimethyltetrahydro 1,3,5-2H-thiadiazine-2-thione as an active constituent; Biochek® 410 (25%wt. actives) (Calgon Corp., Pittsburgh, Pa.) described to be based on 1,2-dibromo-2,4-dicyanobutane and 1,2-benzisothiazolin-3-one and to have an aqueous solubility of 0.22%wt. in water at 25° C.; as well as compounds which are based on metals or metal salts including preparations such as Bactekiller® (Kanebo Chem. Co.) which is described to be a preparation which contains a mixture of silver, zinc and copper metals or metal salts.

As noted previously those which exhibit the relatively low aqueous solubility at 25° C. particularly in the weight ranges and preferred weight ranges are to be preferred. Others, materials although not particularly recited here may be used, and mixtures of two or more biocidal compositions may be used.

An exemplary and preferred material which is commercially available is Tektamer® 38 (98%wt. actives) (Calgon Corporation, Pittsburgh, Pa.) which is cited as exhibiting an aqueous solubility of about 0.22%wt. in water at 25° C.; it is believed that the active constituent in this biocidal composition is 1,2-dibromo-2,4-dicyanobutane. This low aqueous soluble biocidal composition also desirably features a low toxicity profile and thus its use in the household does not expect it to be particularly deleterious to the occupants. This low aqueous soluble biocidal composition also desirably exhibits good compatibility with a broad range of surfactant compositions especially anionic and nonionic surfactants which are optionally included in the articles according to the invention.

The wiping articles according to the invention, and especially the hydrophilic sponges which are the preferred embodiments of the invention may be prepared by any of a number of conventional techniques including but not limited to: spraying the biocidal composition onto or into a wiping article, dipping or soaking the wiping article into a liquid carrier containing the biocial composition, or even supplying the biocidal composition in a process step wherein the wiping articles, particularly sponges, are formed. An exemplary process is one according to the following process. A quantity of the low aqueous soluble biocidal composition is dissolved in a suitable solvent to which the biocidal composition exhibits a higher affinity (than to water), organic solvents such as alcohols, glycols, glycol ethers, and the like, which may also include minor amounts of water. Mixtures of such organic solvents or organic/aqueous solvent compositions, may also be used. Next, a quantity of the low aqueous soluble biocidal composition is dispersed, or dissolved therein. Next, the wiping article intended to be impregnated, especially a sponge, is then immersed within the solvent and biocidal composition and allowed to fully entrain the composition. Thereafter, the wiping article is withdrawn, the solvent is then substantially driven off (which may require mild heating, drawing of a vacuum, or merely permitting it to sit in the ambient environment). Depending upon the volatility of the organic solvent, such may evaporate readily into the air. Optionally, although not always desirably, the wiping article may be first compressed such as through pinch rollers, wrung, or squeezed in order to dry off as much as possible of the organic solvent containing the preservative composition. However, as this concomitantly causes a net loss of the organic solvent with the biocidal composition such is not always desirable.

While the efficacy of the biocidal composition selected for use may vary, and that a higher or lower dosing of biocidal composition per unit mass of the wiping article may be required, generally good results have been achieved when at least about 0.005 grams of the biocidal composition based on the weight of the actives of the biocidal composition are present per gram of wiping article based on the dry weight of the wiping article, viz., in a substantially dehydrated state. Preferably from about 0.005 grams to about 0.20 grams of the biocidal composition are present per gram of wiping article, on a dry weight basis, especially where the wiping article is a cellulose sponge. More preferably the biocidal composition, based on the weight percentage of the actives in the selected biocidal composition, is present in amounts of from 0.01 grams to 0.1 grams, still more preferably from 0.02 grams to 0.1 grams per gram of the wiping article, especially sponges, based on the dry weight of the wiping article. It is to be understood that higher dosing of the biocidal composition will also be expected to impart a longer duration of the anti-microbial properties a wiping article prepared according to the present inventive teaching. Illustrative examples of low aqueous soluble biocidal composition dosings are described in the Examples.

As opposed to many of the prior art wiping articles, and in particularly, sponges, the sponges according to the invention feature a long-lasting antimicrobial benefit. A variety of known art sponges, wiping articles, and especially woven or non-woven wiping wipes may be provided with the benefit of a long-lasting antimicrobial benefit by following the present inventive teachings taught herein. In contrast to many of the teachings of the prior art, the selection of the preservative compositions having relatively low aqueous solubility, is not believed to be taught or anticipated in the prior art. The present known art preservative compositions, including antimicrobial quaternary ammonium compounds which are commonly used as preservative agents for sponges, especially cellulose sponges, have an appreciably higher water solubility and thus cannot provide the long-term antimicrobial benefit to the inventive wiping articles. Further, as may be seen from the above description of the invention, there are no particular process steps which need to be following during the manufacture or the formation of the wiping article, i.e., such as the formation of a cellulose sponge according to the viscose process, or in the formation of the woven or non-woven wipe which needs to be followed. All of these articles, however, may be successfully treated in accordance with the process taught herein and be provided with the long-term antimicrobial benefits discussed herein.

Wiping articles according to the invention, and especially those according to the preferred embodiment, i.e., sponges, may include one or more further constituents to enhance the overall performance of properties. One class of materials are compatible surfactants which do not deleteriously effect the overall antimicrobial benefit provided by the biocidal compositions introduced into the wiping article. These may include any of the known classes including anionic, nonionic, cationic, zwitterionic, but are desirably selected from among anionic surfactants or which are known for their good foaming and detergency properties, and from the nonionic surfactants which also provide a degree of foaming and detergency to the articles according to the invention.

Exemplary anionic surface active agents include compounds known to the art as useful as anionic surfactants. These include but are not limited to: alkali metal salts, ammonium salts, amine salts, aminoalcohol salts or the magnesium salts of one or more of the following compounds: alkyl sulfates, alkyl ether sulfates, alkylamidoether sulfates, alkylaryl polyether sulfates, monoglyceride sulfates, alkylsulfonates, alkylamide sulfonates, alkylarylsulfonates, olefinsulfonates, paraffin sulfonates, alkyl sulfosuccinates, alkyl ether sulfosuccinates, alkylamide sulfosuccinates, alkyl sulfosuccinamate, alkyl sulfoacetates, alkyl phosphates, alkyl ether phosphates, acyl sarconsinates, acyl isethionates, and N-acyl taurates. Generally, the alkyl or acyl radical in these various compounds comprise a carbon chain containing 12 to 20 carbon atoms.

Further exemplary anionic surface active agents which may be used include fatty acid salts, including salts of oleic, ricinoleic, palmitic, and stearic acids; copra oils or hydrogenated copra oil acid, and acyl lactylates whose acyl radical contains 8 to 20 carbon atoms.

Other anionic surface active agents not particularly enumerated here may also find use in conjunction with the compounds of the present invention.

With regard to nonionic surfactants, these include known art nonionic surfactant compounds. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic surfactant compound. Further, the length of the polyethenoxy hydrophobic and hydrophilic elements may various. Exemplary nonionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides.

To be mentioned as particularly useful nonionic surfactants are alkoxylated linear primary and secondary alcohols such as those commercially available under the tradenames PolyTergent® SL series (Olin Chemical Co., Stamford Conn.), Neodol® series (Shell Chemical Co., Houston Tex.); as alkoxylated alkyl phenols including those commercially available under the tradename Triton® (X series (Union Carbide Chem. Co., Danbury Conn.).

Where such surfactants are included in the wiping articles of the invention, they may be supplied to the wiping article by any effective means including but not limiting to spraying, dipping, soaking a quantity of one or more surfactants dispersed or dissolved in a suitable carrier liquid which my be made us of water, organic solvents or mixtures thereof or which water is most likely to be used.. Where one or more surfactants are intended to be used, and the carrier liquid is water, it is desired then that the one or more surfactants be supplied to the wiping articles prior to the process for introduction of the low aqueous soluble biocidal composition to the wiping articles as taught herein.

Certain preferred embodiments of the invention, as well as a demonstration of the long-term antimicrobial benefits of the wiping articles according to the invention described in more fully in examples below.

EXAMPLES

The residual long-term antimicrobial benefits of the wiping articles according to the invention are demonstrated in the following.

A side-by-side evaluation of a first set of "control" sponges with a second set of sponges prepared and treated in accordance with the present invention was performed.

The sponges in each of the first and second sets were made of cellulose and were approximately $4^{9/16^{th}}$ of an inch by $3^{1/16^{th}}$ of inch by $^{7/8^{th}}$ of an inch in dimension. These sponges were used as supplied, and had a dry weight (substantially dehydrated weight) of 12.5 grams. It was believed that a minor amount of an aqueous soluble biocidal composition was included in the control sponge (i.e., less than 0.08 grams for the total sponge) as it was supplied by the manufacturer. The presence of this biocidal composition, in small amounts, is intended to resist the growth of yeasts, mold, bacteria and viruses during the shelf-life of the article. The first set of control sponges were used "as is" supplied from the manufacturer.

The second set of sponges were prepared in accordance with the inventive teaching as follows. To a glass beaker was supplied 19 grams of an organic solvent (denatured anhydrous ethanol) to which was added 1.0 gram of a low-aqueous soluble biocidal composition commercially available as Tektamer® 38 (Calgon Corporation, Pittsburgh, Pa.); it is believed that the active constituents in this biocidal composition were 1,2-dibromo-2,4-dicyanobutane as described above. This low-aqueous soluble biocidal composition exhibited an aqueous solubility of less than 1% by weight in water, and further provided the benefits of good compatibility with anionic and nonionic surfactants which may be optionally included in the wiping articles according to the invention. Further, this low-aqueous soluble biocidal composition was recited as being effective against both gram positive and gram negative bacteria, as well as mold and yeasts, and thus considered a "broad spectrum" antimicrobial agent. Additionally, this low-aqueous soluble biocidal composition had a low toxicity profile and thus its use in the household does not expect it to be particularly deleterious to the occupants.

Next, each of the sponges were totally immersed in the organic solvent containing the low-aqueous soluble biocidal composition, and it was retained for sufficient time so that the sponge totally absorbed as much of the said organic solvent and biocidal composition as was feasible. Thereafter, it was withdrawn, laid on a flat non-porous surface, and the organic solvent was permitted to evaporate into the ambient environment. The amount of low-aqueous soluble biocidal delivered to each sponge was 1.0 grams per sponge, which corresponded to a dosing of 0.08 grams of the low-aqueous soluble biocidal composition per gram of the sponge on a dry weight basis. This drying took approximately 24 hours. Thereafter, the sponge was slightly resilient to the touch.

This protocol was repeated for each of the sponges in the second set, and in a sufficient number to perform the test described below.

The evaluation of the residual antimicrobial benefit of the sponges was performed using an inoculum which contained both *Escherichia coli* (gram negative type pathogenic bacteria) (ATCC 8739) and *Salmonella choleraesuis* (gram negative type pathogenic bacteria) (ATCC 10708). The inoculum was prepared from a lyophilized culture of each of the indicated bacteria which was rehydrated and stored on CTA medium. Each bacteria was thereafter cultured in Trypic Soy Broth for each inoculation. During the test protocol, for each inoculation as described below, a fresh preparation of the inoculum described above was used.

The test was performed over a 15 day interval, wherein on sequential days (except for intervening weekend days of Saturday, and Sunday) each sponge in each of the sets of sponges was individually contacted with 1.0 ml of the inoculum containing the *E. coli* and *S. choleraesuis* bacteria at a concentration of log $10^6$ of each bacteria, which had been provided to a sterile hard surface. The sponges absorbed the 1.0 ml of the inoculum. Thereafter, to each of the sponges were further introduced approx. 75 ml. of Trypic Soy Broth in order to facilitate the distribution of the inoculum within the sponge, and an additional approx. 50 ml. amount of sterile deionized water was also added to further moisten the sponge and aid in distributing the inoculum within. Thereafter, each sponge was then manually wrung to remove any excess liquid, and then laid on a non-porous hard surface which was opened to the ambient environment. This protocol was performed on each of the sequential days once in the "am" (between 8–11 AM) and once in the "pm" (between 1–5 PM).

On the days indicated (see Tables 1, 2 and 3), one of the sponges was removed from each of the sets of sponges, and tested in order to determine the presence of the *E. coli* and *S. choleraesuis* bacteria.

In each test, the respective sponges were cut in half, and shortly thereafter (approx. 15 minutes to 60 minutes) one half of each sponge was therafter put through a Stomacher apparatus (Model 400 commercially available from the Tekmar Co.) to which was supplied 200 ml of Letheen broth. The stomacher was operated for a period of approximately 5 minutes, after which an aliquot of the Letheen broth was removed, serially diluted according to conventional techniques, and plated with a sterile agar medium. The aliquot of the Letheen broth was presumed to contain any *E. coli* and *S. choleraesuis* bacteria which may have been present in the sponge.

The other half of the sponge was tested in a similar manner, but were first permitted to remain on a hard surface in the laboratory and was tested on the next successive day when tests were performed, and are indicated as "am" sponges on the Tables 1, 2 and 3. This permitted for the remaining half sponge to remain in the ambient and to permit any present *E. coli* and *S. choleraesuis* bacteria to grow within the sponge. Thus, it should be understood that the test results associated with a half sponge listed as an "am" half sponge is the remaining half of the half sponge tested in the "pm" of the day prior, or in the case of intervening weekend days, was from the Friday prior.

The aliquot thus removed was used, in accordance with conventional techniques, to produce dilutions at each of $1\times10^{-2}$ through $1\times10^{-7}$ which were then plated with sterile MacConkey Agar. These plates were permitted to incubate for 36–48 hours at 35° C.–37° C. so to permit the growth of colonies of any *Escherichia coli* and/or *Salmonella choleraesuis* bacteria which may have been present.

The protocol described above was repeated for various days of the test. It is further to be appreciated that the sponges in the latter part of the test had been contacted for each of the days indicated above, and thus these sponges had undergone repeated cycles of contact, wringing out, lay in the ambient, until their day arrived and they were tested by being cut apart and extracted in the Letheen broth from which the number of colonies of any *Escherichia coli* and/or *Salmonella choleraesuis* bacteria which may have been present were ultimately evaluated. The results of these evaluations are indicated on Table 1, and on Table 2, below.

TABLE 1

Sponges treated with Quaternary Ammonium Chloride (Control)

| Day | $10^{-2}$ | $10^{-3}$ | $10^{-4}$ | $10^{-5}$ | $10^{-6}$ | $10^{-7}$ | Organisms/ ½ Sponge | Organisms/ Sponge |
|---|---|---|---|---|---|---|---|---|
| 1 pm | TNTC | 12 | 3 | 0 | 0 | 0 | $1.2 \times 10^4$ | $2.4 \times 10^4$ |
| 2 am | 6 | 2 | 0 | 0 | 0 | 0 | $6.0 \times 10^2$ | $1.2 \times 10^3$ |
| 3 pm | TNTC | TNTC | 45 | 6 | 0 | 0 | $4.5 \times 10^5$ | $9.0 \times 10^5$ |
| 4 am | TNTC | TNTC | 13 | 0 | 0 | 0 | $1.3 \times 10^5$ | $2.6 \times 10^5$ |
| 5 pm | TNTC | TNTC | TNTC | TNTC | 25 | 1 | $2.5 \times 10^7$ | $5.0 \times 10^7$ |
| 8 am | TNTC | TNTC | TNTC | TNTC | TNTC | TNTC | $>3.0 \times 10^9$ | $>6.0 \times 10^9$ |
| 8 pm | TNTC | TNTC | TNTC | TNTC | TNTC | TNTC | $>3.0 \times 10^9$ | $>6.0 \times 10^9$ |
| 9 am | TNTC | TNTC | TNTC | TNTC | TNTC | TNTC | $>3.0 \times 10^9$ | $>6.0 \times 10^9$ |
| 10 pm | TNTC | TNTC | TNTC | TNTC | TNTC | TNTC | $>3.0 \times 10^9$ | $>6.0 \times 10^9$ |
| 11 am | TNTC | TNTC | TNTC | TNTC | TNTC | TNTC | $>3.0 \times 10^9$ | $>6.0 \times 10^9$ |
| 12 pm | TNTC | TNTC | TNTC | TNTC | TNTC | TNTC | $>3.0 \times 10^9$ | $>6.0 \times 10^9$ |
| 15 am | TNTC | TNTC | TNTC | TNTC | TNTC | TNTC | $>3.0 \times 10^9$ | $>6.0 \times 10^9$ |

TNTC = to numerous to count

TABLE 2

Sponge treated with 1,2-dibromo-2,4-dicyanobutane (Invention)

| Day | $10^{-2}$ | $10^{-3}$ | $10^{-4}$ | $10^{-5}$ | $10^{-6}$ | $10^{-7}$ | Organisms/ ½ Sponge | Organisms/ Sponge |
|---|---|---|---|---|---|---|---|---|
| 1 pm | 0 | 0 | 0 | 0 | 0 | 0 | <100 | <100 |
| 2 am | 0 | 0 | 0 | 0 | 0 | 0 | <100 | <100 |
| 3 pm | 0 | 0 | 0 | 0 | 0 | 0 | <100 | <100 |
| 4 am | 0 | 0 | 0 | 0 | 0 | 0 | <100 | <100 |
| 5 pm | 0 | 0 | 0 | 0 | 0 | 0 | <100 | <100 |
| 8 am | 0 | 0 | 0 | 0 | 0 | 0 | <100 | <100 |
| 9 am | 3 | 1 | 1 | 0 | 0 | 0 | <100 | <100 |
| 10 pm | 54 | TNTC | 157 | 24 | 0 | 0 | $1.5 \times 10^6$ | $3.0 \times 10^6$ |
| 11 am | TNTC | 39 | 4 | 0 | 0 | 0 | $3.9 \times 10^4$ | $7.8 \times 10^4$ |
| 12 pm | 103 | 132 | 32 | 6 | 0 | 0 | $3.2 \times 10^5$ | $6.4 \times 10^5$ |
| 15 am | 0 | 0 | 0 | 0 | 0 | 0 | <100 | <100 |

TNTC = to numerous to count

As seen from the results indicated on Table 1 (control) and Table 2 (invention) the striking differences between the long-term antimicrobial efficacy of the sponges are demonstrated. As may be denoted from the results on Table 1, while the control sponge exhibited antimicrobial efficacy on the first and second day of the test, thereafter, it can be seen that the antimicrobial efficacy of the sponge substantially degraded thereafter and thus provided effectively no antimiocrobial benefit. Such demonstrates that the use of such commonly encountered preservative constituents, and the dosage ranges commonly encountered of the use of these materials provides a little lasting antimicrobial benefit to the sponge under conditions typically encountered.

In contrast, as a review of the results on Table 2 demonstrate, it may be seen that the sponge treated with the low-aqueous soluble preservative composition, as described above provided a striking and substantial level of efficacy against the *Escherichia coli* and/or *Salmonella choleraesuis* bacteria throughout 15 days of the test, and under the test conditions as described above.

Unlike many of the test protocols which were cited in one or more of the prior art patents, it is believed that the test protocol described herein provides a very useful and realistic test which demonstrates the unexpected and superior properties of the sponges according to the present invention. It is believed by the inventors that the performance of the test upon successive days during a two-week interval and submitting for repeated dosings with the gram negative bacteria noted above, and the demonstration of the strikingly effective long-term antimicrobial characteristics of the sponges are not believed to have been known or readily producible from the prior art.

What is claimed is:

1. A sponge, non-woven wiping article or woven wiping article which is impregnated only with a biocidal composition having an aqueous solubility of not more than 2%wt so as to provide a sponge, non-woven wiping article or woven wiping article having a residual antimicrobial benefit.

2. A sponge, non-woven wiping article or woven wiping article according to claim 1 wherein the biocidal composition has an aqueous solubility of not more than 1.5%wt.

3. A sponge, non-woven wiping article or woven wiping article according to claim 2 wherein the biocidal composition has an aqueous solubility of not more than 1.0%wt.

4. A sponge, non-woven wiping article or woven wiping article according to claim 1 wherein the biocidal composition is present in an amount of from 0.05 g to 1.0 g per gram of the sponge, non-woven wiping article or woven wiping article on a dry weight basis.

5. A process for providing long-lasting residual antimicrobial benefit to a sponge, non-woven or woven wipe, or other wiping article which comprises the process steps of:
   providing a biocidal composition having an aqueous solubility of not more than 2%wt. in an appropriate fluid carrier composition within which said biocidal composition composition is miscible or is soluble,
   impregnating the said wiping article to provide an effective dosage of the preservative composition to the same, and
   subsequently removing the said fluid carrier composition.

6. A sponge, non-woven wiping article or a woven wiping article having a residual antimicrobial benefit produced by the process of:

providing a sponge, non-woven wiping article or a woven wiping article;

subsequently providing a low aqueous soluble biocidal composition in an appropriate fluid carrier in which the biocidal composition is miscible or soluble;

impregnating the sponge, non-woven or woven wipe or other wiping article with said low aqueous soluble biocidal composition in an appropriate fluid carrier; and, subsequently removing a substantial portion of the fluid carrier from the sponge, non-woven wiping article or a woven wiping article.

7. A sponge, non-woven wiping article or woven wiping article which according to claim 6 which comprises:

a low aqueous soluble biocidal composition having an aqueous solubility of not more than 2%wt.

8. A sponge, non-woven wiping article or woven wiping article according to claim 7 which comprises:

a low aqueous soluble biocidal composition having an aqueous solubility of not more than 1.5%wt.

9. A sponge, non-woven wiping article or woven wiping article according to claim 8 which comprises:

a low aqueous soluble biocidal composition having an aqueous solubility of not more than 1.0%wt.

10. A sponge, non-woven wiping article or woven wiping article according to claim 7 wherein the low aqueous soluble biocidal composition absorbed within the sponge, non-woven wiping article or woven wiping article is present in an amount of from 0.05 g to 1.0 g per gram of the sponge, non-woven wiping article or woven wiping article on a dry weight basis.

* * * * *